US00PP27727P2

(12) United States Plant Patent
Sakazaki

(10) Patent No.: US PP27,727 P2
(45) Date of Patent: Feb. 28, 2017

(54) ***PETUNIA* PLANT NAMED 'USTUN69002'**

(50) Latin Name: *Petunia×hybrida*
Varietal Denomination: USTUN69002

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 14/756,439

(22) Filed: Sep. 4, 2015

(51) Int. Cl.
*A01H 5/02* (2006.01)

(52) U.S. Cl.
USPC ..... Plt./356.18

(58) Field of Classification Search
USPC ..... Plt./356.1, 356.18
See application file for complete search history.

*Primary Examiner* — Susan McCormick Ewoldt
(74) *Attorney, Agent, or Firm* — C. A. Whealy

(57) ABSTRACT

A new and distinct *Petunia* plant named 'USTUN69002', characterized by its compact, outwardly spreading and mounding plant habit; freely branching habit; vigorous growth habit; early and freely flowering habit; lavender pink-colored flowers with yellow green-colored centers; and good garden performance.

1 Drawing Sheet

Botanical designation: *Petunia×hybrida.*
Cultivar denomination: 'USTUN69002'.

BACKGROUND OF THE INVENTION

The present invention relates to a new and distinct cultivar of *Petunia* plant, botanically known as *Petunia×hybrida* and hereinafter referred to by the name 'USTUN69002'.

The new *Petunia* plant is a product of a planned breeding program conducted by the Inventor in Higashiomi, Shiga, Japan and Bonsall, Calif. The objective of the breeding program is to create new freely-branching and uniformly mounding *Petunia* plants with early and freely flowering habit, unique attractive flowers and good garden performance.

The new *Petunia* plant originated from a cross-pollination made by the Inventor on May 20, 2012 in Higashiomi, Shiga, Japan of *Petunia×hybrida* 'Bluetta Pink Morn', not patented, as the female, or seed, parent with *Petunia× hybrida* 'Little Holiday Pink Morn', not patented, as the male, or pollen, parent. The new *Petunia* plant was discovered and selected by the Inventor as a single flowering plant within the progeny of the stated cross-pollination in a controlled greenhouse environment in Bonsall, Calif. on Jun. 5, 2013.

Asexual reproduction of the new *Petunia* plant by vegetative terminal cuttings in a controlled greenhouse environment in Bonsall, Calif. since Jun. 6, 2013 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN69002'. These characteristics in combination distinguish 'USTUN69002' as a new and distinct *Petunia* plant:

1. Compact, outwardly spreading and mounding plant habit.
2. Freely branching habit.
3. Vigorous growth habit.
4. Early and freely flowering habit.
5. Lavender pink-colored flowers with yellow green-colored centers.
6. Good garden performance.

Plants of the new *Petunia* can be compared to plants of the female parent, 'Bluetta Pink Morn'. In side-by-side comparisons, plants of the new *Petunia* differ primarily from plants of 'Bluetta Pink Morn' in plant habit as plants of the new *Petunia* are more compact than plants of 'Bluetta Pink Morn'. In addition, plants of the new *Petunia* have slightly smaller flowers than plants of 'Bluetta Pink Morn'.

Plants of the new *Petunia* can be compared to plants of the male parent, 'Little Holiday Pink Morn'. In side-by-side comparisons, plants of the new *Petunia* differ primarily from plants of 'Little Holiday Pink Morn' in the following characteristics:

1. Plants of the new *Petunia* are more mounding than and not as trailing as plants of 'Little Holiday Pink Morn'.
2. Plants of the new *Petunia* have slightly larger flowers than plants of 'Little Holiday Pink Morn'.
3. Plants of the new *Petunia* have better weather tolerance than plants of 'Little Holiday Pink Morn'.

Plants of the new *Petunia* can be compared to plants of 'Opera Supreme Pink Morn', not patented. In side-by-side comparisons, plants of the new *Petunia* differed primarily from plants of 'Opera Supreme Pink Morn' in flower color as plants of 'Opera Supreme Pink Morn' had pink-colored flowers with white and yellow-colored centers. In addition, plants of the new *Petunia* had smaller flowers than plants of 'Opera Supreme Pink Morn'.

Plants of the new *Petunia* can also be compared to plants of 'Storm Pink Morn', not patented. In side-by-side comparisons, plants of the new *Petunia* differed primarily from plants of 'Storm Pink Morn' in flower color as plants of 'Storm Pink Morn' had soft pink-colored flowers with white and yellow-colored centers. In addition, plants of the new *Petunia* had smaller flowers than plants of 'Storm Pink Morn'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'USTUN69002' grown in a container.

The photograph at the top of the sheet is a close-up view of a typical flowering plant of 'USTUN69002'.

DETAILED BOTANICAL DESCRIPTION

The aforementioned photographs and following observations, measurements and values describe plants grown during the summer in 10-cm containers in an outdoor nursery in Bonsall, Calif. During the production of the plants, day temperatures ranged from 18° C. to 34° C., night temperatures ranged from 9° C. to 18° C. and light levels ranged from 7,000 to 10,000. Plants were 8.5 weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN69002'.

Parentage:

*Female, or seed, parent.*—*Petunia×hybrida* 'Bluetta Pink Morn', not patented.

*Male, or pollen, parent.*—*Petunia×hybrida* 'Little Holiday Pink Morn', not patented.

Propagation:

*Type.*—Terminal vegetative cuttings.

*Time to produce a rooted young plant, summer.*—About 15 days at temperatures ranging from 17° C. to 29° C.

*Time to produce a rooted young plant, winter.*—About 20 days at temperatures ranging from 17° C. to 21° C.

*Root description.*—Medium in thickness, fibrous; white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, outwardly spreading and mounding plant habit; freely branching habit with about 24 primary lateral branches with multiple secondary lateral branches developing per plant; dense and bushy appearance; pinching enhances development of lateral branches; vigorous growth habit.

*Plant height.*—About 20.5 cm.

*Plant diameter (area of spread).*—About 32 cm.

*Lateral branches.*—Length: About 20 cm. Diameter: About 3.5 mm. Internode length: About 2.4 cm. Strength: Strong. Aspect: Initially upright then outwardly spreading. Texture: Pubescent, minute. Luster: Matte. Color: Close to 146B.

Leaf description:

*Arrangement.*—Alternate before flowering; opposite after flowers develop; leaves simple.

*Length.*—About 4 cm.

*Width.*—About 1.8 cm.

*Shape.*—Elliptical.

*Apex.*—Acute.

*Base.*—Attenuate.

*Margin.*—Entire.

*Texture, upper and lower surfaces.*—Pubescent.

*Luster, upper and lower surfaces.*—Matte.

*Venation pattern.*—Pinnate, arcuate.

*Color.*—Developing leaves, upper surface: Close to 146B. Developing leaves, lower surface: Close to 146C. Fully expanded leaves, upper surface: Close to N137A; venation, close to 146C. Fully expanded leaves, lower surface: Close to 146A; venation, close to 146C.

*Petioles.*—Length: About 8 mm. Diameter: About 2.5 mm. Strength: Strong. Texture, upper and lower surfaces: Pubescent, minute. Luster, upper and lower surfaces: Matte. Color, upper and lower surfaces: Close to 146B.

Flower description:

*Flower type and flowering habit.*—Single axillary salverform flowers; flowers face mostly upward to outwardly; freely flowering habit with about 17 to 18 flower buds and open flowers per lateral branch and more than 500 flowers developing per plant.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About four to five days; flowers persistent.

*Fragrance.*—None detected.

*Flower buds.*—Length: About 3.4 cm. Diameter: About 6 mm. Shape: Oblong, elongate. Color: Close to 145A.

*Flower diameter.*—About 3 cm.

*Flower depth (height).*—About 4 cm.

*Throat diameter, distal.*—About 7 mm.

*Tube length.*—About 2.7 cm.

*Tube diameter, proximal.*—About 3 mm.

*Petals.*—Quantity and arrangement: Five petals fused in a single salverform whorl. Petal lobe length (from throat): About 1.3 cm. Petal lobe width: About 1.6 cm. Petal lobe shape: Fan-shaped. Petal lobe apex: Rounded with a small point. Petal lobe margin: Shallowly emarginate and slightly sinuate. Petal lobe texture, upper surface: Smooth, glabrous; satiny. Petal lobe texture, lower surface: Pubescent, minute. Throat texture: Smooth, glabrous. Tube texture: Pubescent, minute. Color: When opening, upper surface: Towards the margins, close to 77D; towards the throat, close to 145C. When opening, lower surface: Close to 145C to 145D tinted with close to 76D. Fully opened, upper surface: At the margins, close to 71C; towards the center progressing to closer to 76B;

towards the throat, close to 151D progressing to closer to 145C; venation, close to N144A; color at the margin becoming closer to 77C with development. Fully opened, lower surface: Close to 76C; towards the margins, close to 75D; venation, close to N144A. Flower throat (inside): Close to 151C; venation, close to 144A. Flower tube (outside): Close to 145B; venation, close to 144A.

*Sepals*.—Quantity and arrangement: Five sepals fused in a single star-shaped whorl. Length: About 1.3 cm. Width: About 3 mm. Shape: Lanceolate. Apex: Acute. Margin: Entire. Texture, upper and lower surfaces: Pubescent; minute. Color, upper surface: Close to 147B. Color, lower surface: Close to 146C.

*Peduncles*.—Length: About 2.4 cm. Width: About 2 mm. Strength: Strong. Angle: About 30° to 45° from the stem axis. Texture: Pubescent; minute. Luster: Matte. Color: Close to 146B.

*Reproductive organs*.—Stamens: Quantity per flower: Five. Filament length: About 1.5 cm. Filament color: Close to 145D. Anther length: About 1 mm. Anther shape: Round. Anther color: Close to 160D. Pollen amount: Scarce. Pollen color: Close to 160D. Pistils: Quantity per flower: One. Pistil length: About 1.8 cm. Style length: About 1.5 cm. Style color: Close to 146D. Stigma shape: Round. Stigma color: Close to 146B. Ovary color: Close to 146B.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 3.5° C. to about 43° C.

It is claimed:

1. A new and distinct *Petunia* plant named 'USTUN69002' as illustrated and described.

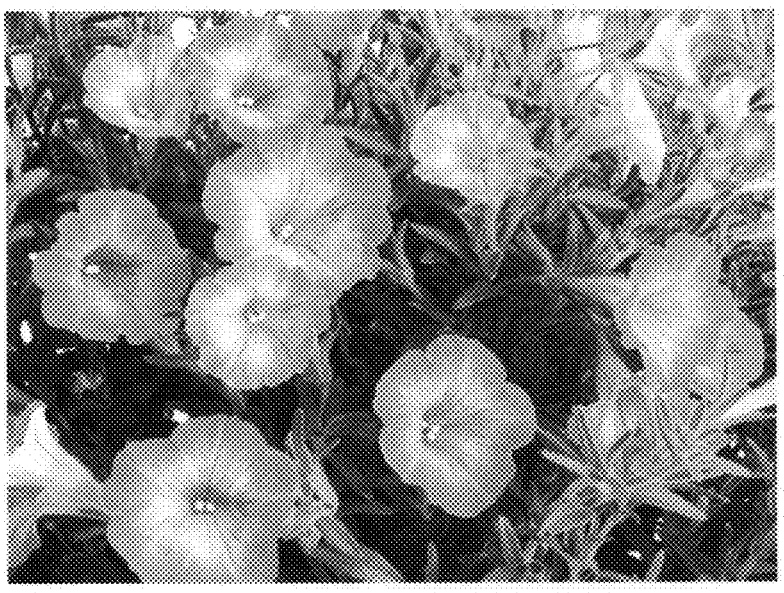
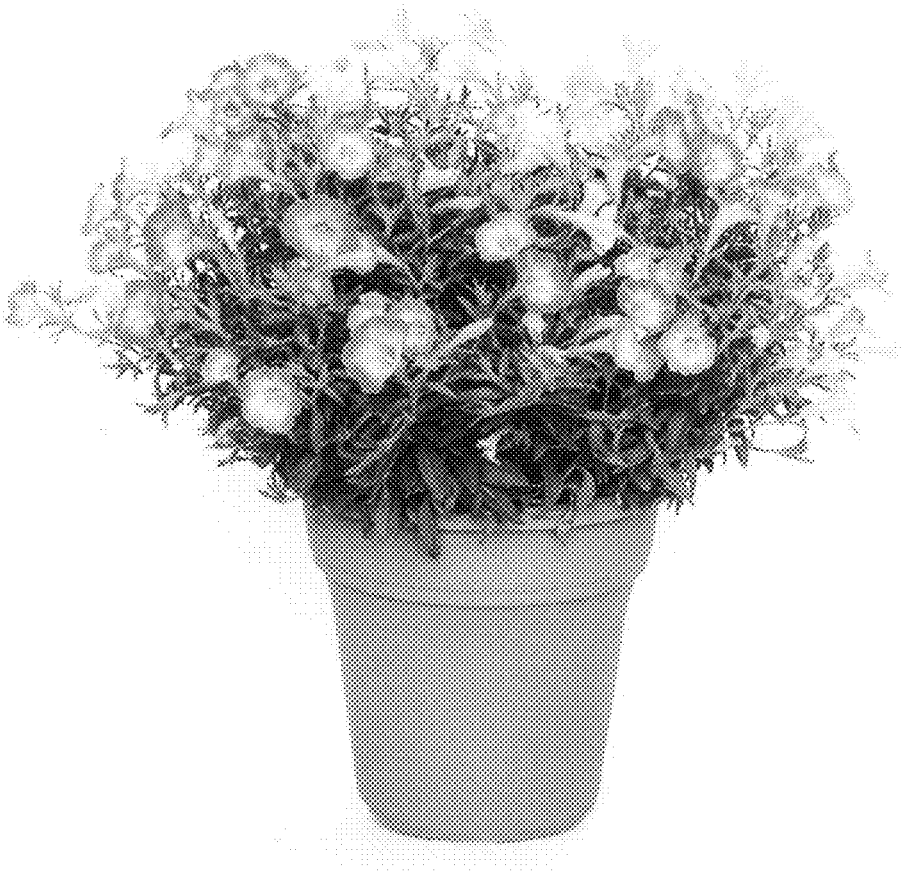

* * * * *